(12) United States Patent
Boecker (10) Patent No.: US 11,579,034 B2
(45) Date of Patent: Feb. 14, 2023

(54) PRESSURE DETECTING UNIT FOR A MEASURING DEVICE FOR MEASURING A PRESSURE STATUS VALUE OF A PLANT SPECIMEN, AND METHOD FOR MANUFACTURING A PRESSURE DETECTING UNIT

(71) Applicant: Robert Bosch GmbH, Stuttgart (DE)

(72) Inventor: Matthias Boecker, Reutlingen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 17/291,363

(22) PCT Filed: Jan. 14, 2020

(86) PCT No.: PCT/EP2020/050765
§ 371 (c)(1),
(2) Date: May 5, 2021

(87) PCT Pub. No.: WO2020/148254
PCT Pub. Date: Jul. 23, 2020

(65) Prior Publication Data
US 2022/0003622 A1  Jan. 6, 2022

(30) Foreign Application Priority Data
Jan. 15, 2019 (DE) .......................... 102019200378.8

(51) Int. Cl.
*G01L 11/00* (2006.01)
*A01G 7/00* (2006.01)
(Continued)

(52) U.S. Cl.
CPC .............. *G01L 11/004* (2013.01); *A01G 7/00* (2013.01); *G01L 9/008* (2013.01); *G01L 19/147* (2013.01); *G01N 33/0098* (2013.01)

(58) Field of Classification Search
CPC ......... A01G 7/00; G01L 11/004; G01L 9/008; G01L 19/147; G01N 33/0098
See application file for complete search history.

(56) References Cited

U.S. PATENT DOCUMENTS

| 9,756,796 B2 | 9/2017 | Gimenez Calbo |
| 2010/0018295 A1* | 1/2010 | Kunze ...................... A01G 7/00 73/64.45 |

(Continued)

FOREIGN PATENT DOCUMENTS

| CN | 101411299 A | 4/2009 |
| CN | 104749031 A | 7/2015 |

(Continued)

OTHER PUBLICATIONS

English Translation of Written Opinion filed May 5, 2021 in U.S. Appl. No. 17/291,363, for PCT/EP2020/050765 (pp. 4-6) (Year: 2020).*

(Continued)

*Primary Examiner* — Ryan D Walsh
(74) *Attorney, Agent, or Firm* — Norton Rose Fulbright US LLP; Gerard Messina (57) ABSTRACT

A method for manufacturing a pressure detecting unit for a measuring device for measuring a pressure status value of a plant specimen. The method includes mounting a sensor unit for detecting the pressure status value at a carrier substrate, fastening a frame to the carrier substrate, the frame including a fastening surface, a contact surface oriented opposite the fastening surface and an inner surface defining an opening and extending between the fastening surface and the contact surface, the frame being situated at the carrier substrate in such a way that the fastening surface faces the carrier substrate and the inner surface surrounds the sensor unit, and filling the opening of the frame with a filling material for forming an elastic pressure coupling layer. A pressure (Continued)

detecting unit for a measuring device for measuring a pressure status value of a plant specimen is also described.

13 Claims, 5 Drawing Sheets

(51) Int. Cl.
　　*G01L 19/14*　　　(2006.01)
　　*G01N 33/00*　　　(2006.01)
　　*G01L 9/00*　　　　(2006.01)

(56) References Cited

U.S. PATENT DOCUMENTS

2011/0049264 A1* 3/2011 Zimmermann ......... G01L 9/008
　　　　　　　　　　　　　　　　　　　　　　　　239/266
2013/0305831 A1 11/2013 Zimmermann et al.

FOREIGN PATENT DOCUMENTS

| DE | 102006043058 A1 | 3/2008 | |
|----|----|----|----|
| DE | 102009032872 A1 | 1/2011 | |
| EP | 2244548 A1 | 11/2010 | |
| EP | 2672806 A2 | 12/2013 | |
| WO | 2009092389 A1 | 7/2009 | |
| WO | WO-2011006620 A1 * | 1/2011 | ............... A01G 7/00 |
| WO | 2012107555 A2 | 8/2012 | |

OTHER PUBLICATIONS

International Search Report for PCT/EP2020/050765, dated Mar. 17, 2020.

* cited by examiner

PRESSURE DETECTING UNIT FOR A MEASURING DEVICE FOR MEASURING A PRESSURE STATUS VALUE OF A PLANT SPECIMEN, AND METHOD FOR MANUFACTURING A PRESSURE DETECTING UNIT

BACKGROUND INFORMATION

Hydrostatic overpressure in plant cells is referred to as turgor pressure and represents a parameter for evaluating a status, in particular an irrigation status, of a plant. By detecting the turgor pressure or a turgor pressure-dependent pressure status value, for example at leaves of the plant, conclusions may be drawn as to whether the water supply of the plant is sufficient or an irrigation of the plant is necessary.

To measure the turgor pressure or a variable representing the turgor pressure of a plant specimen, for example a leaf of the plant, measuring devices are being increasingly used, which are based on a non-destructive or non-invasive measuring method. For this purpose, the plant specimen is typically clamped with the aid of a clamping device, and a pressure signal representing the turgor pressure is registered with the aid of a sensor unit.

German Patent Application No. DE 10 2006 043 058 A1 describes a measuring device for measuring a pressure status value of a plant, including a pressure detecting unit, which includes a plate-shaped sensor carrier having a recess open on one side and a sensor unit situated on the bottom of the recess, the recess being filled with an elastic pressure coupling layer made from silicone. To measure the pressure status value, the plant specimen is pressed against the pressure coupling layer of the measuring device with the aid of a clamping part, so that the sensor unit may detect a pressure. German Patent Application No. DE 10 2009 032 872 A1 describes a similar pressure detecting unit, a sensor unit being glued to the bottom of a recess of a sensor clamping block and being wired in the recess. A filling of the recess with a casting compound then takes place to form a pressure coupling layer. A further pressure detecting unit of this type is described in European Patent No. EP 2 244 548 B1.

European Patent No. EP 2 672 806 B1 describes a pressure detecting unit for measuring a turgor pressure of a plant with the aid of a sensor fitting and a sensor unit accommodated in a recess of the sensor fitting. The sensor unit includes a circuit board, at which a pressure sensor is situated, the sensor insert being cast in a polymer material in the recess. To manufacture the measuring unit, the sensor unit is inserted into the recess in the sensor fitting and subsequently cast layer by layer with polymer material.

SUMMARY

The present invention relates to a method and a pressure detecting unit.

According to a first aspect of the present invention, a method is provided for manufacturing a pressure detecting unit for a measuring device for measuring a pressure status value of a plant specimen. The pressure status value may be formed by a turgor pressure of the plant specimen or a status variable dependent on the turgor pressure.

In accordance with an example embodiment of the present invention, the method includes a mounting of a sensor unit for detecting the pressure status value on a carrier substrate. The carrier substrate may be implemented, in particular, as a planar plate, the sensor unit being configured to detect a pressure and being fastened to a mounting surface of the carrier substrate, e.g., soldered or glued thereto.

After mounting the sensor unit, a fastening of a frame to the carrier substrate takes place, the frame including a fastening surface, a contact surface oriented opposite the fastening surface and an inner surface defining an opening and extending between the fastening surface and the contact surface, the frame being situated at the carrier substrate in such a way that the fastening surface faces the carrier substrate, and the inner surface surrounds the sensor unit. In this step, the frame, which has a through-opening extending between a first surface or contact surface and a second surface or fastening surface situated opposite thereto, is placed on the mounting surface of the carrier substrate in such a way that the sensor unit is situated in the opening of the frame, and the fastening surface of the frame faces the carrier substrate. In particular, the fastening surface of the frame may be connected to the mounting surface of the carrier substrate. The contact surface is used for contact with and for clamping the plant specimen.

In a further step, a filling of the opening of the frame with a filling material takes place to form an elastic pressure coupling layer. For this purpose, the filling material is supplied in a viscous elastic or pourable state to the opening of the frame and fills it at least partially, preferably completely, so that the sensor unit situated in the opening is completely embedded into the filling material. The filling material is provided for contact with the plant specimen and is used to transfer a pressure force of the plant specimen to the sensor unit.

According to a second aspect of the present invention, a pressure detecting unit for a measuring device is provided for measuring a pressure status value of a plant specimen. The pressure detecting unit according to this aspect of the present invention may be manufactured, in particular, using a method according to the first aspect of the present invention. The features and advantages of the method described in the present description thus similarly apply to the pressure detecting device and vice versa.

In accordance with an example embodiment of the present invention, the pressure detecting device includes a carrier substrate, a sensor unit situated at the carrier substrate for detecting the pressure status value, and a frame fastened to the carrier substrate, which includes a fastening surface facing the carrier substrate, a contact surface oriented opposite the fastening surface for contact with the plant specimen, and an inner surface defining an opening and extending between the fastening surface and the contact surface, the inner surface surrounding the sensor unit. The frame is therefore implemented as a separate component from the carrier substrate, which includes a through-opening, within which the sensor unit is situated.

The pressure detecting unit further includes an elastic pressure coupling layer, which fills the opening, for contact with the plant specimen for transferring a force to the sensor unit. The pressure coupling layer is formed from an elastic filling material, for example a silicone material or a polymer material, into which the sensor unit situated in the opening is completely embedded. The pressure coupling layer preferably forms a coupling surface, which uniformly continues the contact surface of the frame, in particular in a planar manner.

In accordance with the present invention, a pressure detecting unit for a measuring device is implemented for measuring a turgor pressure-dependent pressure status value of a plant specimen, including a carrier substrate or a carrier plate, on which a pressure sensor unit is mounted, and a frame, separate from the carrier substrate or the carrier plate, which has a through-opening. As a result, the sensor unit for detecting the pressure status value may be fastened to the mounting surface of the carrier substrate before the frame is attached. This makes it easier to mount the sensor unit. In addition, the opening of the frame may be made smaller, or the inner surface, which defines the opening and surrounds the sensor unit, may be situated at a minimal distance from the sensor unit, without making it more difficult to mount the sensor unit. A smaller diameter or a smaller cross-sectional area of the opening reduces the force necessary for generating a certain pressure, by means of which a clamping force with which the pressure detecting unit is pressed against the plant specimen may be decreased. This reduces both the risk of damaging the plant and the risk of the sensor unit becoming damaged.

Advantageous designs and refinements of the present invention result from the disclosure herein.

According to one specific embodiment of the method in accordance with the present invention, it is provided that the mounting of the sensor unit includes a fastening of the sensor unit to the carrier substrate and a contacting of the sensor unit. The fastening of the sensor unit may include, in particular, a gluing, a soldering, a clipping on or a similar integral or form-fitting fastening of the sensor unit to the mounting surface of the carrier substrate. For the purpose of contacting, electrical terminals provided at the sensor unit are electrically connected to electrical terminals provided at the carrier substrate, e.g., via wire or strip conductor structures.

According to a further specific embodiment of the method in accordance with the present invention, the filling material is introduced into the opening of the frame in a pourable state and hardened in the opening. The hardening of the filling material may include, in particular, a cross-linking reaction, by means of which the elastic properties of the filling material or the pressure coupling layer are advantageously settable.

According to a further specific embodiment of the method in accordance with the present invention, the filling material is introduced into the opening of the frame from a front side defined by the contact surface of the frame. In this way, the opening is successively filled, starting at the mounting surface of the carrier substrate, by means of which a uniform filling is advantageously achieved, reducing the risk of the formation of air bubbles or other inclusions. The frame may optionally include ventilation channels extending from or defined by the inner surface, which further reduce the risk of air inclusions.

According to a further specific embodiment of the method in accordance with the present invention, it is provided that the frame is fastened to the carrier substrate in an integral manner, in particular by gluing, or in a form-fitting manner, in particular by a clip connection. An integral connection offers, in particular, the advantage that the fastening surface of the frame is particularly reliably sealed against the carrier substrate. A form-fitting connection may be mounted, for example, very quickly and easily.

According to one specific embodiment of the pressure detecting device in accordance with the present invention, it is provided that the inner surface defines a first diameter or a first cross-sectional area of the opening, in the area of the contact surface of the frame, in particular at the contact surface, and defines a second diameter or a second cross-sectional area of the opening, in the area of the fastening surface of the frame, in particular at the fastening surface, the second diameter or the second cross-sectional area being larger than the first diameter or the first cross-sectional area of the opening. The opening thus narrows from the carrier substrate or the fastening surface in the direction of the contact surface. The inner surface thus forms an undercut with respect to an axis situated perpendicularly to the contact surface. In this way, an obstacle is implemented by the inner surface, which counteracts a movement of the pressure coupling layer out of the opening. This is advantageous, in particular, if the contact surface is at a distance from the plant specimen. Particularly elastic or soft pressure coupling layers may thus be used, which cling very effectively to the plant specimen. The accuracy of the measurement results is increased thereby. Furthermore, the deformation of the pressure coupling layer is reduced when it is detached from the plant specimen, by means of which the risk of a damage to the sensor unit is decreased. In addition, the cross section or diameter of the opening, which expands from the contact surface in the direction of the fastening surface or the carrier substrate, offers the advantage that a large mounting surface for the sensor unit is provided at the carrier substrate. At the same time, however, a contact surface of the pressure coupling layer for contact with the plant specimen may be reduced, whereby only a low force is necessary to generate a predefined contact pressure, and the pressure detecting unit may furthermore be attached to smaller leaves without problems.

To implement different diameters or cross-sectional surfaces at the contact surface and the fastening surface, the inner surface may extend in an inclined or angled manner, at least in sections, relative to an axis extending transversely or perpendicularly to the contact surface. For example, the inner surface may define a circular opening, the inner surface defining a frustoconical cross section of the opening, at least in sections. A frustoconical geometry of this type offers the advantage that it may be particularly easily and thus cost-effectively manufactured by machining methods. Of course, the inner surface may also define triangular, rectangular or polygonal opening cross sections, the inner surface defining a pyramid-shaped or generally truncated polyhedron-shaped cross section, at least in sections.

According to a further specific embodiment of the pressure detecting unit in accordance with the present invention, it is provided that the carrier substrate is formed by a circuit board. This makes it easier, in particular, to contact or wire the sensor unit.

According to a further specific embodiment of the pressure detecting unit in accordance with the present invention, the sensor unit includes a sensor element for detecting the pressure status value and for generating a pressure signal representing the turgor pressure or the pressure status value in the form of a MEMS structure, and includes a readout unit in the form of an ASIC for processing the pressure signal which may be generated by the sensor element. "MEMS" stands for the expression "microelectronic and microelectromechanical system." "ASIC" is an abbreviation for the expression "application-specific integrated circuit." The pressure signal provided by the sensor element may be digitized by the ASIC directly in the sensor unit. In particular, the MEMS structure may be advantageously contacted or wired via the ASIC. The mounting of the sensor unit is thus further simplified. Using a circuit board as the carrier substrate also results in the advantage that common soldering processes may be used for wiring and fastening the sensor unit implemented by a MEMS structure and an ASIC, by means of which an easy and cost-effective mounting is made easier.

According to a further specific embodiment of the pressure detecting unit in accordance with the present invention, it is provided that the frame includes a magnetic or magnetizable material. For example, the frame may be assembled from a base part, which provides or forms the contact surface, the fastening surface and the inner surface of the frame defining the opening, and a magnet part made from a magnetizable or magnetic material, the magnet part being accommodated in a receiving structure, e.g., a receiving groove of the base part. For example, the base part may be manufactured from a plastic material. Alternatively, the frame as a whole may be formed from a magnetic or magnetizable material.

According to a further specific embodiment of the pressure detecting unit in accordance with the present invention, it is provided that the frame is formed from a plastic material. In particular, thermoplastic materials, thermosetting materials or elastomer materials may be considered here.

The frame may generally include, for example, a rectangular, circular, polygonal or similar outer circumference. The outer circumference of the frame is implemented by an outer circumferential surface situated opposite the inner surface, which extends between the fastening surface and the contact surface of the frame. The outer circumference surface may extend, for example, in parallel to the inner surface.

With respect to direction indications and axes, in particular with respect to direction indications and axes relating to the course of physical structures, a course of an axis, a direction or a structure "along" another axis, direction or structure is understood to be the fact that it, in particular the tangents resulting in a particular location of the structures, each run at an angle of less than 45 degrees, preferably less than 30 degrees and particularly preferably in parallel to each other.

With respect to direction indications and axes, in particular with respect to direction indications and axes relating to the course of physical structures, a course of an axis, a direction or a structure "transverse" to another axis, direction or structure is understood to be the fact that it, in particular the tangents resulting in a particular location of the structures, each run at an angle of greater than or equal to 45 degrees, preferably greater than or equal to 60 degrees and particularly preferably perpendicular to each other.

A "plant specimen" herein is understood to be a constituent part of an intact plant, in particular a plant organ or plant tissue, for example a leaf or a stem of the plant. The constituent part of the plant may have been separated from the rest of the plant.

The present invention is explained in greater detail below on the basis of the exemplary embodiments shown in the schematic figures.

DETAILED DESCRIPTION OF EXAMPLE EMBODIMENTS

Figure 1:
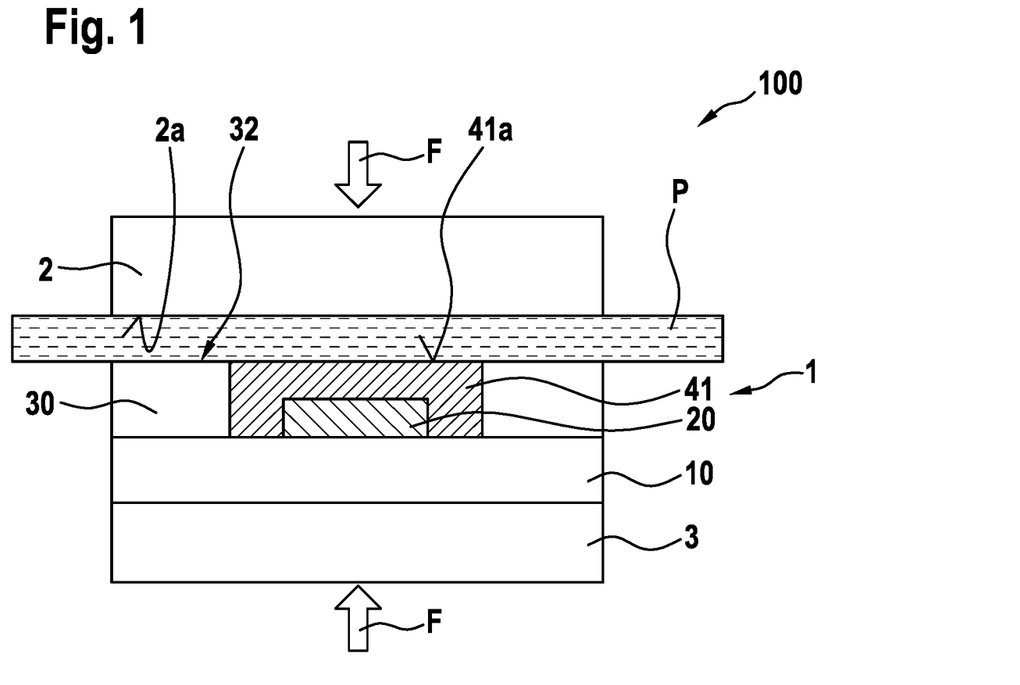
FIG. 1 shows a schematic sectional view of a measuring device for measuring a pressure status value of a plant specimen, which includes a pressure detecting unit according to one exemplary embodiment of the present invention.

FIG. 1 schematically shows a sectional view of a measuring device 100 for measuring a pressure status value of a plant specimen P. The measured pressure status value is dependent on the so-called turgor pressure of plant specimen P. The hydrostatic overpressure in plant cells is referred to as turgor pressure and is a parameter representing an irrigation status of the plant. A high turgor pressure typically represents a high water content and thus a sufficient irrigation status of the plant, while a low turgor pressure indicates a low water content in the plant. Measuring device 100 illustrated as an example in FIG. 1 includes a pressure detecting unit 1 and a clamping unit 2. A magnet 3 may also be optionally provided.

As schematically illustrated in FIG. 1, pressure detecting unit 1, which is explained in detail below, includes a carrier substrate 10, a sensor unit 20, a frame 30 and a pressure coupling layer 41.

Clamping unit 2 is implemented as a plate-shaped component, which includes a clamping contact surface 2a. Clamping unit 2 may be formed, in particular, partially or entirely from a magnetic or magnetizable material, and is used as a counter-bearing for clamping a plant specimen P, as illustrated as an example in FIG. 1.

To measure the pressure status value, a plant specimen P, e.g., a leaf of a plant, is clamped between clamping contact surface 2a of clamping unit 2 and a contact surface 32 of frame 30 of pressure detecting unit 1, as illustrated schematically in FIG. 1. A predetermined clamping force F is applied to the plant specimen, which is applied, for example, by a magnetic force acting upon clamping unit 2 by optional magnet 3. The pressure coupling medium or pressure coupling layer 41, which is elastically deformable, thereby comes into contact with plant specimen P with a contact surface 41a and may thereby transfer a pressure force to sensor unit 20. Sensor unit 20 thereby detects a variable representing the pressure status value or the turgor pressure.

Different pressure detecting units 1 are shown in FIGS. 2 through 5, which may be used to detect a pressure status value, as described above. As illustrated as an example in FIG. 2, pressure detecting unit 1, includes a carrier substrate 10, a sensor unit 20, a frame 30 and a pressure coupling layer 41.

Figure 2:
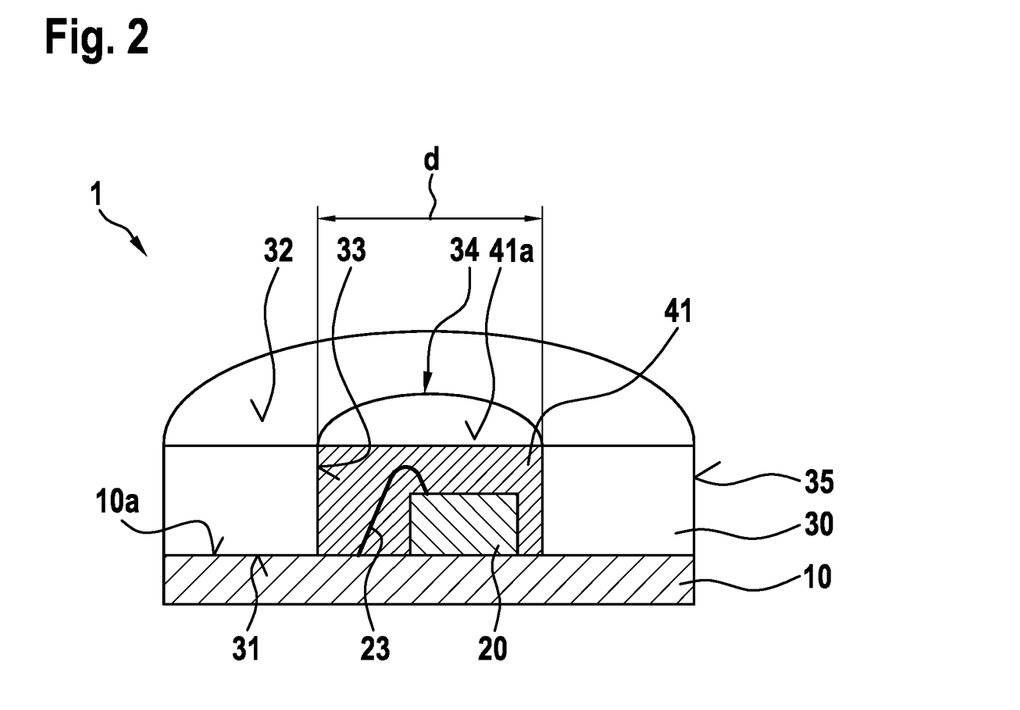
FIG. 2 shows a perspective view of a schematic sectional representation of a pressure detecting unit according to one exemplary embodiment of the present invention.

As is apparent in the perspective sectional view in FIG. 2, carrier substrate 10 may be implemented as a disk having a circular outer circumference. Of course, other circumferential geometries are also possible. Carrier substrate 10 is generally implemented as a planar, plate-shaped component, which provides a mounting surface 10*a*. Carrier substrate 10 is used as a carrier or holder for the further components of the pressure detecting unit. Carrier substrate 10 may optionally be implemented as a circuit board, on which electrical contact points or contacting structures are formed, such as strip conductors (not illustrated) or the like.

Figure 5:
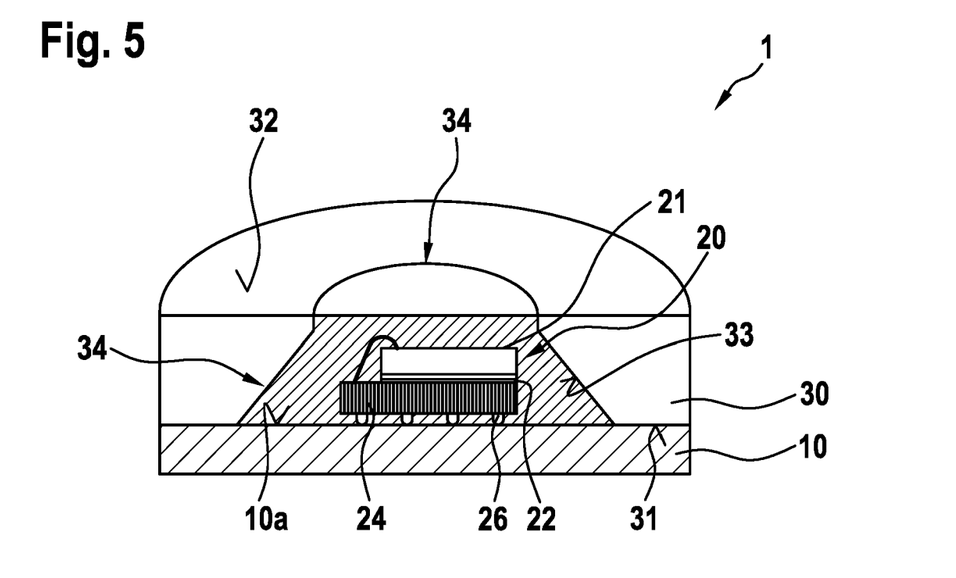
FIG. 5 shows a perspective view of a schematic sectional representation of a pressure detecting unit according to a further exemplary embodiment of the present invention.

Sensor unit 20 is illustrated only schematically as a block in FIG. 2. Sensor unit 20 is generally implemented as a force/pressure sensor, which is configured to detect a variable representing a pressure. As illustrated schematically in FIG. 5, sensor unit 20 may include a sensor element 21 for detecting the pressure status value and for generating a pressure signal, which represents the pressure status value or the turgor pressure and is implemented as a MEMS structure. The MEMS structure may include, for example, a carrier chip including a deformable diaphragm mounted thereon, electrical resistors being mounted on the diaphragm, which are interconnected to form a Wheatstone bridge. Due to a deformation of the diaphragm as a result of a pressure change, an electrical voltage change occurs in proportion to the deformation, which is represented as a variable representing a pressure signal. As is also illustrated in FIG. 5, a readout unit 22 may be optionally provided in addition to sensor element 21 in the form of an ASIC for processing the pressure signal which may be generated by the sensor element. As is further illustrated in FIG. 5, readout unit 22 and sensor element 21 may be situated and contacted on a shared sensor circuit board 24. Alternatively, pressure sensors of other designs may be used, whose pressure signal is further processed or evaluated at an external readout unit.

As is schematically illustrated in FIG. 2, sensor unit 20 is situated at carrier substrate 10, in particular at mounting surface 10*a* of carrier substrate 10. For example, sensor unit 20 may be glued or soldered at mounting surface 10*a*. As is also schematically illustrated in FIG. 2, sensor unit 20 is electrically contacted via a wiring 23, e.g., to connecting structures (not illustrated) provided at carrier substrate 10. As illustrated as an example in FIG. 5, a contacting and fastening of sensor circuit board 24 may be simultaneously implemented by solder connections 26.

Figure 6:
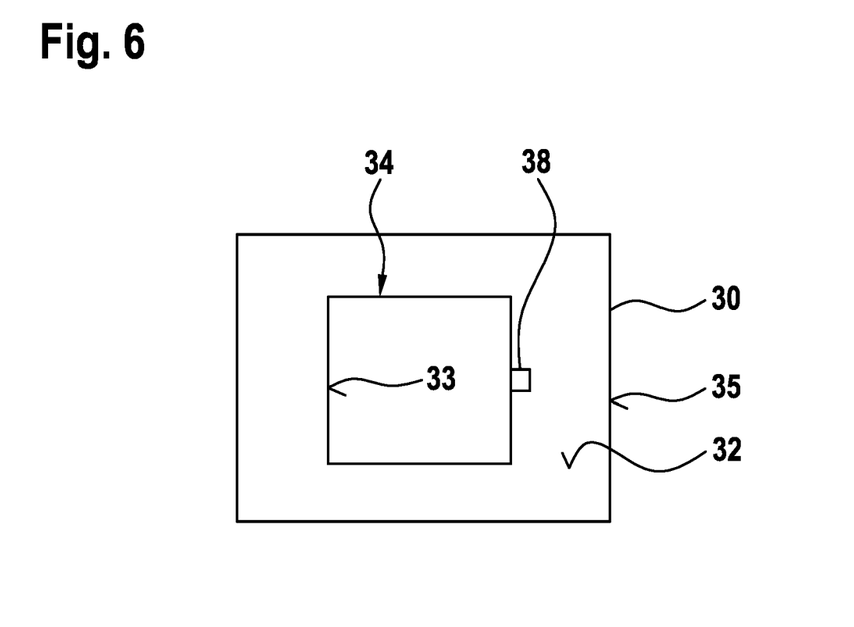
FIG. 6 shows a top view of a contact surface of a frame of a pressure detecting unit according to a further exemplary embodiment of the present invention.

As is further illustrated in FIG. 2, frame 30 may be implemented as a circular ring-shaped component. FIG. 6, on the other hand, schematically shows a top view of a frame 30, which is implemented with a rectangular outer circumference and a rectangular opening 34. Frame 30 generally includes a fastening surface 31, a contact surface 32 oriented opposite fastening surface 31, an inner surface 33 defining an opening 34 and extending between fastening surface 31 and contact surface 32, and an outer circumferential surface 35 oriented opposite inner surface 33 and extending between fastening surface 31 and contact surface 32.

Fastening surface 31 and contact surface 32 may be, in particular, planar and preferably extend in parallel to each other, as illustrated schematically in FIG. 2. Contact surface 32 is used for contact with plant specimen P, as was explained on the basis of FIG. 1. Fastening surface 31 of frame 30 is used to connect or fasten frame 30 to mounting surface 10*a* of carrier substrate 10. Outer circumferential surface 35 connects fastening surface 31 to contact surface 32 and thereby defines the circumferential geometry of frame 30. As illustrated in FIGS. 2 through 5, outer circumferential surface 35 may define, for example, a circular outer circumference of frame 30. A rectangular outer circumference of frame 30, which is defined by outer circumferential surface 35, is illustrated as an example in FIG. 6. Of course, other circumferential geometries of frame 30 are also possible, e.g., an oval, a triangular, a trapezoidal or other polygonal outer circumferences. The fact that inner surface 33 and outer circumferential surface 35 extend in parallel to each other is illustrated as an example in FIGS. 2 through 6. It is, of course, also possible that inner surface 33 and outer circumferential surface 35 define different geometries of opening 34 and the outer circumference.

As further illustrated in FIG. 2, inner surface 33 connects fastening surface 31 to contact surface 32 and thereby forms a through-opening 34 of frame 30 extending between fastening surface 31 and contact surface 32. Inner surface 33 further defines the cross-sectional shape of opening 34. For example, opening 34 may have a circular cross section, e.g., a cylindrical cross section, as illustrated schematically in FIG. 2. Of course, other cross-sectional shapes are also possible, for example a rectangular cross section, as illustrated as an example in FIG. 6. Other polygonal cross-sectional shapes are also possible.

FIG. 2 shows an example of a frame 30, whose inner surface 33 defines a constant cross section or diameter d of opening 34. As illustrated as an example in FIGS. 3 through 5, it may also be provided that a diameter defined by inner surface 33 or a cross-sectional surface of opening 34 defined by inner surface 33 increases from contact surface 32 in the direction of fastening surface 31.

Figure 3:
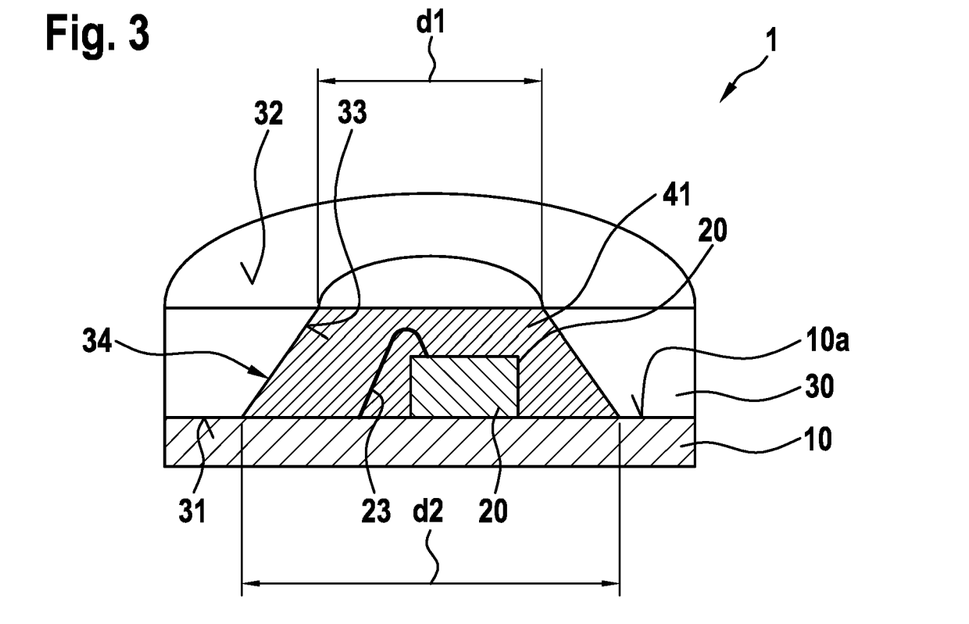
FIG. 3 shows a perspective view of a schematic sectional representation of a pressure detecting unit according to a further exemplary embodiment of the present invention.

FIG. 3 shows an example of the fact that inner surface 33 defines a frustoconical cross section of the opening, a first diameter d1 or a first cross-sectional surface of opening 34 at contact surface 32 being smaller than a second diameter d2 or a second cross-sectional surface of opening 34 at fastening surface 31.

Figure 4:
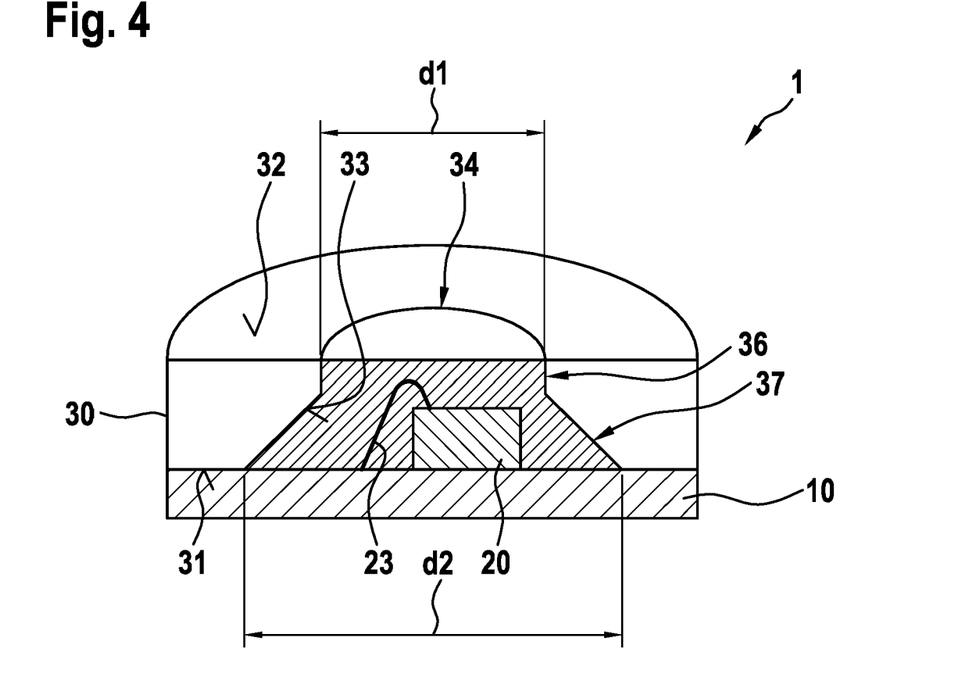
FIG. 4 shows a perspective view of a schematic sectional representation of a pressure detecting unit according to a further exemplary embodiment of the present invention.

A partially frustoconical cross section of opening 34 is illustrated as an example in FIGS. 4 and 5. In particular, inner surface 33 defines a cylindrical cross-sectional area 36 of opening 34 including a first diameter d1 in the area of contact surface 32 and a frustoconical area 37 extending between this cylindrical area 36 and fastening surface 31, opening 34 including a second diameter d2 at fastening surface 32, which is larger than first diameter d1.

In addition to the cross-sectional profiles illustrated as an example in FIGS. 3 through 5, other profiles are also possible, e.g., a truncated pyramid-shaped profile or a truncated pyramid-shaped profile at least in sections. Inner surface 33 of frame 30 generally defines a first diameter d1 or a first cross-sectional surface of opening 34 in the area of contact surface 32 of frame 30 and a second diameter d2 or a second cross-sectional surface of opening 34 in the area of fastening surface 31 of frame 30, second diameter d2 or the second cross-sectional surface being larger than first diameter d1 or the first cross-sectional surface of opening 34.

Frame 30 may include a magnetic or magnetizable material or be formed from a material of this type. In this case, magnet 3 may be advantageously dispensed with, if clamping unit 2 of measuring device 100 is implemented as a magnet. Frame 30 may also be formed from a plastic material, e.g., from a thermoplastic material, a thermosetting material or an elastomer. It is also possible that magnetic or magnetizable material areas are introduced into the plastic material.

Frame 30 is fastened at carrier substrate 10 in such a way that fastening surface 31 faces mounting surface 10*a* of carrier substrate 10, and sensor unit 20 is situated in opening 34 of frame 30. Inner surface 33 thus surrounds sensor unit 20, as illustrated schematically in FIGS. 2 through 5. For example, frame 30 may be glued to carrier substrate 10 or fastened thereto in a form-fitting manner, e.g., by a clip connection.

Pressure coupling layer 41 is situated in opening 34 of frame 30. In particular, opening 34 may be completely filled by pressure coupling layer 41, as illustrated as an example in FIGS. 2 through 5. As is apparent in FIGS. 2 through 5, it may be provided that a contact surface 41a formed by pressure coupling layer 41, which is situated facing away from carrier substrate 10 and is provided for contact with plant specimen P, extends in a planar manner to contact surface 31 of frame 30. Pressure coupling layer 41 is formed from an elastically deformable filling material 40, e.g., a silicone material or a polymer material, and is used to transfer a force to sensor unit 20, as was explained above in connection with FIG. 1.

As is apparent in FIGS. 3 through 5, sufficient space for the sensor unit may be provided at mounting surface 10a of carrier substrate 10 by the diameter or cross-sectional surface of opening 34, which increases in size from contact surface 32 of frame 30 in the direction of fastening surface 31, while opening 34 has a smaller diameter d1 at contact surface 31. To generate a certain pressure at contact surface 41a of pressure coupling layer 41, whose size is defined by first diameter d1 of opening 34, only a low force is therefore advantageously necessary. In addition, pressure coupling layer 41 is held in opening 34 in a form-fitting manner due to the diameter of opening 34, which grows smaller in the direction of contact surface 31.

FIGS. 7 through 10 schematically show an example of a method for manufacturing a pressure detecting unit 1 for a measuring device 100 for measuring a pressure status value of a plant specimen P. The method is suitable, in particular, for manufacturing pressure detecting unit 1 described above and is explained below with reference to pressure detecting unit 1 described above. The features and advantages described in connection with pressure detecting unit 1 thus apply similarly to the method and vice versa.

Figure 7:
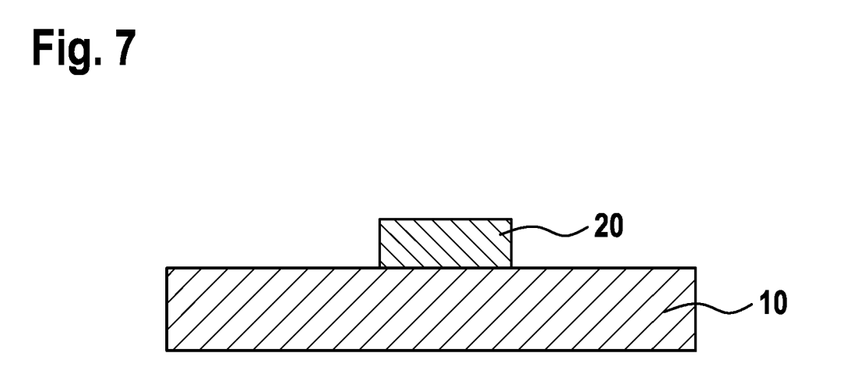
FIG. 7 shows a first step of a method for manufacturing a pressure detecting unit according to one exemplary embodiment of the present invention.
Figure 8:
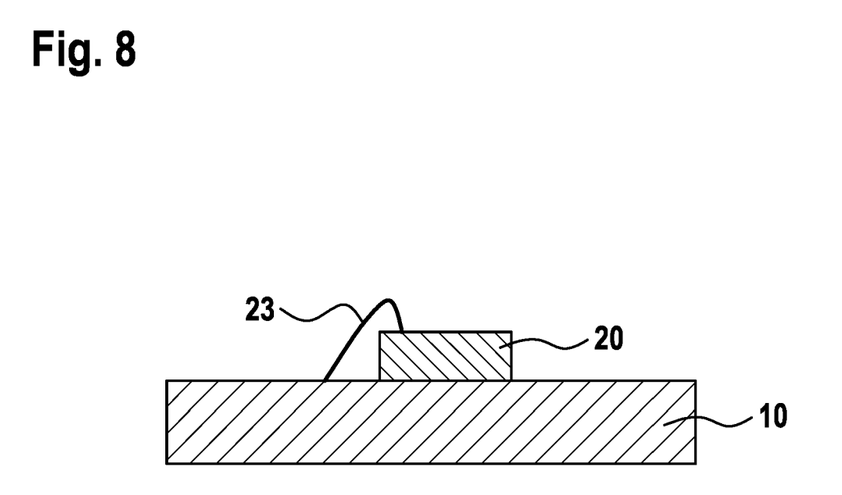
FIG. 8 shows a further step of the method according to one exemplary embodiment of the present invention.

As illustrated in FIG. 7, a mounting of sensor unit 20 at carrier substrate 10 takes place initially. For example, sensor unit 20 may be glued or soldered to mounting surface 10a of carrier substrate 10 or otherwise fastened thereto. The mounting of sensor unit 20 may already include a contacting of sensor unit 20, e.g., if it is designed as shown in FIG. 5 and is soldered to carrier substrate 10. Alternatively, the contacting takes place after the fastening, as illustrated as an example in FIG. 8, sensor unit 20 being electrically contacted, for example via a wiring 23, e.g., to connecting structures (not illustrated) provided at carrier substrate 10.

Figure 9:
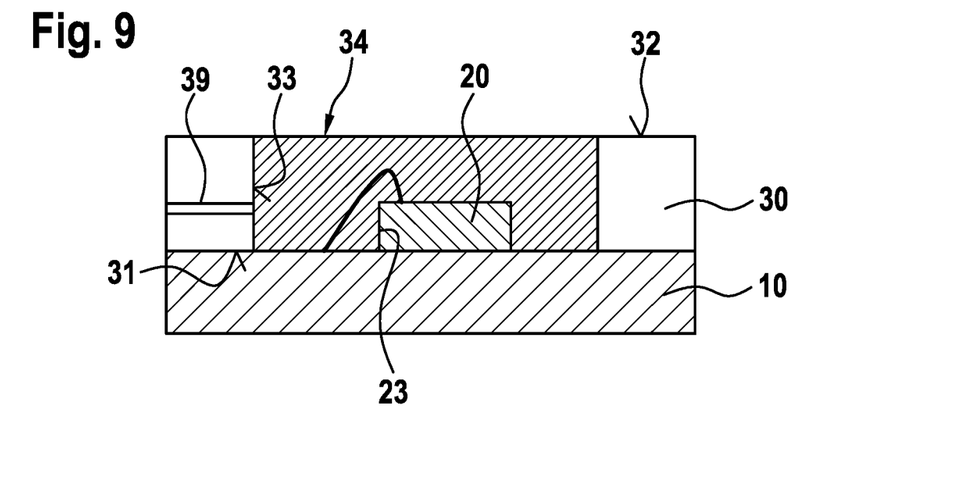
FIG. 9 shows a further step of the method according to one exemplary embodiment of the present invention.

After mounting sensor unit 20, a fastening of frame 30 at carrier substrate 10 takes place, as illustrated as an example in FIG. 9. Frame 30 is placed with fastening surface 31 on mounting surface 10a of carrier substrate 10 and positioned on mounting surface 10a of carrier substrate 10 in such a way that inner surface 33 surrounds sensor unit 20. Frame 30 and the sensor unit are thus mounted at carrier substrate 10 separately from each other. In particular, sensor unit 20 is fastened and electrically contacted first, and frame 30 is subsequently set in place. Opening 34 of frame 30 may therefore be relatively small, since no mounting space must be provided for inserting mounting devices which hold sensor device 20. This makes it easier to automate the method. At the same time, a more compact design of pressure detecting unit 1 may be implemented.

Frame 30 may generally be fastened at carrier substrate 10 in an integral manner, for example by gluing, or in a form-fitting manner, for example by a clip connection.

A filling of opening 34 of frame 30 with filling material 40 then takes place to form elastic pressure coupling layer 41. This step is illustrated schematically in FIG. 10. Filling material 40 is introduced into opening 34 of frame 30 in a pourable state. After the introduction, a hardening of filling material 40 in opening 34 takes place, e.g., by a chemical cross-linking reaction. For this purpose, it may be provided, for example, that filling material 40 is brought to a certain temperature after it is introduced into opening 34, or it is irradiated with UV light, to initiate and/or terminate the chemical reaction.

Figure 10:
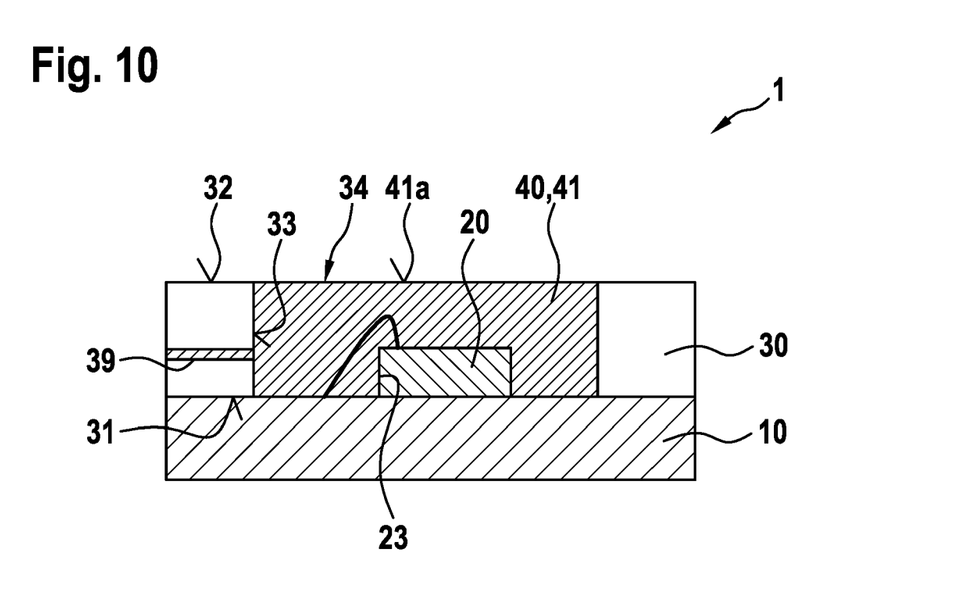
FIG. 10 shows a further step of the method according to one exemplary embodiment of the present invention.

Filling material 40 may be filled, in particular, directly into opening 34, i.e., from a front side defined by contact surface 32 of frame 30. To prevent air inclusions, frame 30 may include optional ventilation structures, e.g., in the form of a venting channel 39 extending from inner surface 33 to the outer circumferential surface 35, as illustrated in FIGS. 9 and 10, and/or in the form of a venting groove 38, as illustrated schematically in FIG. 6, which is formed at inner surface 33 and extends up to contact surface 31 of frame 30.

Although the present invention was fully described above on the basis of preferred exemplary embodiments, it is not limited thereto, but may be modified in many ways.

What is claimed is:

1. A method for manufacturing a pressure detecting unit for a measuring device for measuring a pressure status value of a plant specimen, the method comprising the following steps:

mounting a sensor unit, configured to detect the pressure status value, at a mounting surface of a carrier substrate;

fastening a frame to and on the mounting surface of the carrier substrate, the frame including a fastening surface, a contact surface oriented opposite the fastening surface, and an inner surface which defines an opening and extends between the fastening surface and the contact surface, the frame being situated at the carrier substrate in such a way that the fastening surface faces the carrier substrate, and the inner surface surrounds the sensor unit; and filling the opening of the frame with a filling material for forming an elastic pressure coupling layer.

2. The method as recited in claim 1, wherein the mounting of the sensor unit includes an electrical contacting of the sensor unit with connecting structures provided at the carrier substrate.

3. The method as recited in claim 1, wherein the filling material is introduced into the opening of the frame in a pourable state and is hardened in the opening.

4. The method as recited in claim 1, wherein the filling material is inserted into the opening of the frame from a front side defined by the contact surface of the frame.

5. The method as recited in claim 1, wherein the frame is fastened at the mounting surface of the carrier substrate in an integral manner by gluing, or in a form-fitting manner by a clip connection.

6. The method as recited in claim 1, wherein the frame includes at least one venting channel extending from the inner surface to an outer circumferential surface of the frame and/or at least one venting groove formed at the inner surface and extending up to the contact surface of the frame.

7. A pressure detecting unit for a measuring device for measuring a pressure status value of a plant specimen, comprising:

a carrier substrate including a mounting surface;

a sensor unit situated at the mounting surface of the carrier substrate, the sensor unit configured to detect the pressure status value;

a frame fastened to and on the mounting surface of the carrier substrate, the frame having a fastening surface facing the carrier substrate, a contact surface oriented opposite the fastening surface for contact with the plant specimen, and an inner surface which defines an opening and extends between the fastening surface and the contact surface, the inner surface surrounding the sensor unit; and an elastic pressure coupling layer filling the opening for contact with the plant specimen to transfer a force to the sensor unit.

8. The pressure detecting unit as recited in claim 7, wherein the inner surface defines a first cross-sectional surface of the opening in an area of the contact surface of the frame, and a second cross-sectional surface of the opening in the area of the fastening surface of the frame, the second cross-sectional surface being larger than the first cross-sectional surface of the opening.

9. The pressure detecting unit as recited in claim 7, wherein the carrier substrate is a circuit board.

10. The pressure detecting unit as recited in claim 7, wherein the sensor unit includes a sensor element configured to detect the pressure status value and to generate a pressure signal representing the pressure status value, the sensor element being in the form of a MEMS structure, and includes a readout unit in the form of an ASIC for processing the pressure signal which may be generated by the sensor element.

11. The pressure detecting unit as recited in claim 7, wherein the frame includes a magnetic or magnetizable material.

12. The pressure detecting unit as recited in claim 7, wherein the frame is formed from a plastic material, the plastic material being a thermoplastic material, or a thermosetting material, or an elastomer material.

13. The pressure detecting unit as recited in claim 7, wherein the frame includes at least one venting channel extending from the inner surface to an outer circumferential surface of the frame and/or at least one venting groove formed at the inner surface and extending up to the contact surface of the frame.

* * * * *